(12) United States Patent
Mabrouk et al.

(10) Patent No.: US 7,285,621 B2
(45) Date of Patent: *Oct. 23, 2007

(54) MULTIPLE BRANCH PEPTIDE CONSTRUCTION

(75) Inventors: Kamel Mabrouk, Les Pennes-Mirabeau (FR); Jean-Marc Sabatier, Rousset (FR); Herve Rochat, Mimet (FR); Jurphaas Van Rietschoten, Aix-en-Provence (FR)

(73) Assignee: Ambrilia Biopharma, Verdun, Quebec (CA)

( * ) Notice: Subject to any disclaimer, the term of this patent is extended or adjusted under 35 U.S.C. 154(b) by 1048 days.

This patent is subject to a terminal disclaimer.

(21) Appl. No.: 10/126,915

(22) Filed: Apr. 19, 2002

(65) Prior Publication Data

US 2006/0155108 A1    Jul. 13, 2006

Related U.S. Application Data

(63) Continuation-in-part of application No. 09/342,847, filed on Jun. 29, 1999, now Pat. No. 6,379,679.

(51) Int. Cl.
*A61K 38/04* (2006.01)
*C07K 5/00* (2006.01)
*C07K 7/00* (2006.01)
*C07K 17/00* (2006.01)

(52) U.S. Cl. ..................................... 530/328
(58) Field of Classification Search ............... None
See application file for complete search history.

(56) References Cited

FOREIGN PATENT DOCUMENTS

WO        WO98/29443    *  6/1998

* cited by examiner

*Primary Examiner*—Bruce R. Campell
*Assistant Examiner*—Nicole E Kinsey
(74) *Attorney, Agent, or Firm*—Cherskov & Flaynik

(57) ABSTRACT

Multiple branch peptide constructions formed from peptide-branches derived from the envelope transmembrane glycoprotein gp41 of HIV, and including the consensus sequence RQGY preceded by 0 to 4 amino acid residues and succeeded by 0 to 4 amino acid residues, most preferably RQGYS, show increased receptor affinity and prevent cell-to-cell fusion. They have a direct virostatic effect. Because they present the same peptide sequence several times, these MBPCs are able to neutralize in vitro the different steps of virus envelope/cell membrane fusion, and infected cell membrane/uninfected cell membrane fusion of several strains of HIV-1 and HIV-2. These results open a potential use in treatment of HIV infection.

15 Claims, 3 Drawing Sheets

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: Not Applicable
      (D) TOPOLOGY: linear (ii) MOLECULE TYPE: Genomic DNA (iii) HYPOTHETICAL: yes (xi) SEQUENCE DESCRIPTION: SEQ ID NO: 1

Arg Gln Gly Tyr
1

(2) INFORMATION FOR SEQ ID NO: 2:

(i) SEQUENCE CHARACTERISTICS:
      (A) LENGTH: 5 amino acids
      (B) TYPE: amino acids
      (C) STRANDEDNESS: Not Applicable
      (D) TOPOLOGY: linear (ii) MOLECULE TYPE: Genomic DNA (iii) HYPOTHETICAL: yes (xi) SEQUENCE DESCRIPTION: SEQ ID NO: 2

Arg Gln Gly Tyr Ser
1              5

(2) INFORMATION FOR SEQ ID NO: 3:

(i) SEQUENCE CHARACTERISTICS:
    (A) LENGTH: 56 amino acids
    (B) TYPE: amino acids
    (C) STRANDEDNESS: Not Applicable
    (D) TOPOLOGY: linear (ii) MOLECULE TYPE: Genomic DNA (iii) HYPOTHETICAL: yes (xi) SEQUENCE DESCRIPTION: SEQ ID NO: 3:

```
Arg Gln Gly Tyr Ser Pro Leu Arg Gln Gly Tyr Ser Pro Leu Arg Gln
1               5                   10                  15

Gly Tyr Ser Pro Leu Arg Gln Gly Tyr Ser Pro Leu Arg Gln Gly Tyr
            20                  25                  30

Ser Pro Leu Arg Gln Gly Tyr Ser Pro Leu Arg Gln Gly Tyr Ser Pro
        35                  40                  45

Leu Arg Gln Gly Tyr Ser Pro Leu
    50                  55
```

(2) INFORMATION FOR SEQ ID NO: 4:

(i) SEQUENCE CHARACTERISTICS:
    (A) LENGTH: 126 amino acids
    (B) TYPE: amino acids
    (C) STRANDEDNESS: Not Applicable
    (D) TOPOLOGY: linear (ii) MOLECULE TYPE: Genomic DNA (iii) HYPOTHETICAL: yes (xi) SEQUENCE DESCRIPTION: SEQ ID NO: 4:

```
Arg Gln Gly Tyr Ser Pro Leu Arg Gln Gly Tyr Ser Pro Leu Arg Gln
1               5                   10                  15

Gly Tyr Ser Pro Leu Arg Gln Gly Tyr Ser Pro Leu Arg Gln Gly Tyr
            20                  25                  30

Ser Pro Leu Arg Gln Gly Tyr Ser Pro Leu Arg Gln Gly Tyr Ser Pro
        35                  40                  45

Leu Arg Gln Gly Tyr Ser Pro Leu Arg Gln Gly Tyr Ser Pro Leu Arg
    50                  55                  60

Gln Gly Tyr Ser Pro Leu Arg Gln Gly Tyr Ser Pro Leu Arg Gln Gly
65                  70                  75                  80

Tyr Ser Pro Leu Arg Gln Gly Tyr Ser Pro Leu Arg Gln Gly Tyr Ser
                85                  90                  95

Pro Leu Arg Gln Gly Tyr Ser Pro Leu Arg Gln Gly Tyr Ser Pro Leu
            100                 105                 110

Arg Gln Gly Tyr Ser Pro Leu Arg Gln Gly Tyr Ser Pro Leu
            115                 120                 125
```

(2) INFORMATION FOR SEQ ID NO: 5:

(i) SEQUENCE CHARACTERISTICS:
    (A) LENGTH: 10 amino acids
    (B) TYPE: amino acids
    (C) STRANDEDNESS: Not Applicable
    (D) TOPOLOGY: linear (ii) MOLECULE TYPE: Genomic DNA (iii) HYPOTHETICAL: yes (xi) SEQUENCE DESCRIPTION: SEQ ID NO: 5:

```
Arg Gln Gly Tyr Ser Arg Gln Gly Tyr Ser
1               5                   10
```

(2) INFORMATION FOR SEQ ID NO: 6:

(i) SEQUENCE CHARACTERISTICS:
        (A) LENGTH: 14 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 6:

```
Arg Gln Gly Tyr Ser Pro Leu Arg Gln Gly Tyr Ser Pro Leu
1               5                   10
```

(2) INFORMATION FOR SEQ ID NO: 7:

(i) SEQUENCE CHARACTERISTICS:
        (A) LENGTH: 32 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 7:

```
Arg Gln Gly Tyr Arg Gln Gly Tyr Arg Gln Gly Tyr Arg Gln Gly Tyr
1               5                   10                  15

Arg Gln Gly Tyr Arg Gln Gly Tyr Arg Gln Gly Tyr Arg Gln Gly Tyr
                20                  25                  30
```

(2) INFORMATION FOR SEQ ID NO: 8:

(i) SEQUENCE CHARACTERISTICS:
        (A) LENGTH: 12 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 8:

```
Arg Gln Gly Tyr Ser Pro Arg Gln Gly Tyr Ser Pro
1               5                   10
```

(2) INFORMATION FOR SEQ ID NO: 9:

(i) SEQUENCE CHARACTERISTICS:
        (A) LENGTH: 8 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 9:

```
Arg Gln Gly Tyr Arg Gln Gly Tyr
1               5
```

(2) INFORMATION FOR SEQ ID NO: 10:

(i) SEQUENCE CHARACTERISTICS:
        (A) LENGTH: 6 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 10:

Arg Gln Gly Arg Gln Gly
1               5

(2) INFORMATION FOR SEQ ID NO: 11:

(i) SEQUENCE CHARACTERISTICS:
        (A) LENGTH: 12 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 11:

Gln Gly Tyr Ser Pro Leu Gln Gly Tyr Ser Pro Leu
1               5                   10

(2) INFORMATION FOR SEQ ID NO: 12:

(i) SEQUENCE CHARACTERISTICS:
        (A) LENGTH: 10 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 12:

Gly Tyr Ser Pro Leu Gly Tyr Ser Pro Leu
1               5                   10

(2) INFORMATION FOR SEQ ID NO: 13:

(i) SEQUENCE CHARACTERISTICS:
        (A) LENGTH: 8 amino acids
        (B) TYPE: amino acids
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 13:

Tyr Ser Pro Leu Tyr Ser Pro Leu
1               5

(2) INFORMATION FOR SEQ ID NO: 14:

(i) SEQUENCE CHARACTERISTICS:
        (A) LENGTH: 6 amino acids
        (B) TYPE: amino acids
        (C) STRANDEDNESS: Not Applicable
        (D) TOPOLOGY: linear

```
        (ii) MOLECULE TYPE: Genomic DNA (iii) HYPOTHETICAL: yes (xi) SEQUENCE DESCRIPTION: SEQ ID NO: 14:

Ser Pro Leu Ser Pro Leu
1               5

(2) INFORMATION FOR SEQ ID NO: 15:

(i) SEQUENCE CHARACTERISTICS:
             (A) LENGTH: 14 amino acids
             (B) TYPE: amino acids
             (C) STRANDEDNESS: Not Applicable
             (D) TOPOLOGY: linear (ii) MOLECULE TYPE: Genomic DNA (iii) HYPOTHETICAL: yes (xi) SEQUENCE DESCRIPTION: SEQ ID NO: 15:

Arg Gln Gly Tyr Ser Pro Leu Arg Gln Gly Tyr Ser Pro Leu
1               5                  10

(2) INFORMATION FOR SEQ ID NO: 16:

(i) SEQUENCE CHARACTERISTICS:
             (A) LENGTH: 14 amino acids
             (B) TYPE: amino acids
             (C) STRANDEDNESS: Not Applicable
             (D) TOPOLOGY: linear (ii) MOLECULE TYPE: Genomic DNA (iii) HYPOTHETICAL: yes (xi) SEQUENCE DESCRIPTION: SEQ ID NO: 16:

Lys Gln Gly Tyr Ser Pro Leu Lys Gln Gly Tyr Ser Pro Leu
1               5                  10

(2) INFORMATION FOR SEQ ID NO: 17:

(i) SEQUENCE CHARACTERISTICS:
             (A) LENGTH: 14 amino acids
             (B) TYPE: amino acids
             (C) STRANDEDNESS: Not Applicable
             (D) TOPOLOGY: linear (ii) MOLECULE TYPE: Genomic DNA (iii) HYPOTHETICAL: yes (xi) SEQUENCE DESCRIPTION: SEQ ID NO: 17:

Arg Gln Gly Tyr Ser Pro Leu Arg Gln Gly Tyr Ser Pro Leu
1               5                  10
```

MULTIPLE BRANCH PEPTIDE CONSTRUCTION

This application is a Continuation-in-Part of the patent application entitled MULTIPLE BRANCH PEPTIDE CONSTRUCTION, (Ser. No. 09/342,847) filed on Jun. 29, 1999 and now U.S. Pat. No. 6,379,679.

BACKGROUND OF THE INVENTION

1. Field of the Invention

The invention relates to multiple branch peptide constructions (MBPCs) and to their use in the treatment of Human Immunodeficiency Virus (HIV) infections.

2. Background of the Invention

The use of radially branched systems in polymers has been known for a long time in classical polymer chemistry. This system has been used by J. P. Tam [*Proc. Natl. Acad. Sci. USA* 85, 5409-5413 (1988)] to develop antigens without the use of ambiguous carriers, using lysine skeletons. Those antigens were designed to generate vaccines against a variety of diseases. Antigens for generating vaccines against HIV infection are described by Tam in WO93/03766. He called them Multiple Antigenic Peptide Systems (MAPS), consistent with their conceived use.

The present inventors, along with others, found that similar constructions with shorter peptides derived from the V3 loop of the surface envelope glycoprotein gp120 of HIV offered a direct therapeutic approach to the treatment of HIV infections, as described in WO95/07929. The name MAPS was then inappropriate, and the compounds were renamed as MBPCs. The MBPCs of WO95/07929 interfered with the virus envelope—cell membrane fusion step and also the infected cell membrane—uninfected cell membrane fusion step, either step being thought to be indispensable for cell infection, virus multiplication and the spread of virus in the host organism, by blockading the CD4 receptor present in cells such as lymphocytes and macrophages, apparently by attaching to a membrane co-receptor which is distinct from the CD4 binding receptor, without causing the cell to lose its ability to be activated by other antigens or mitogens.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1A:
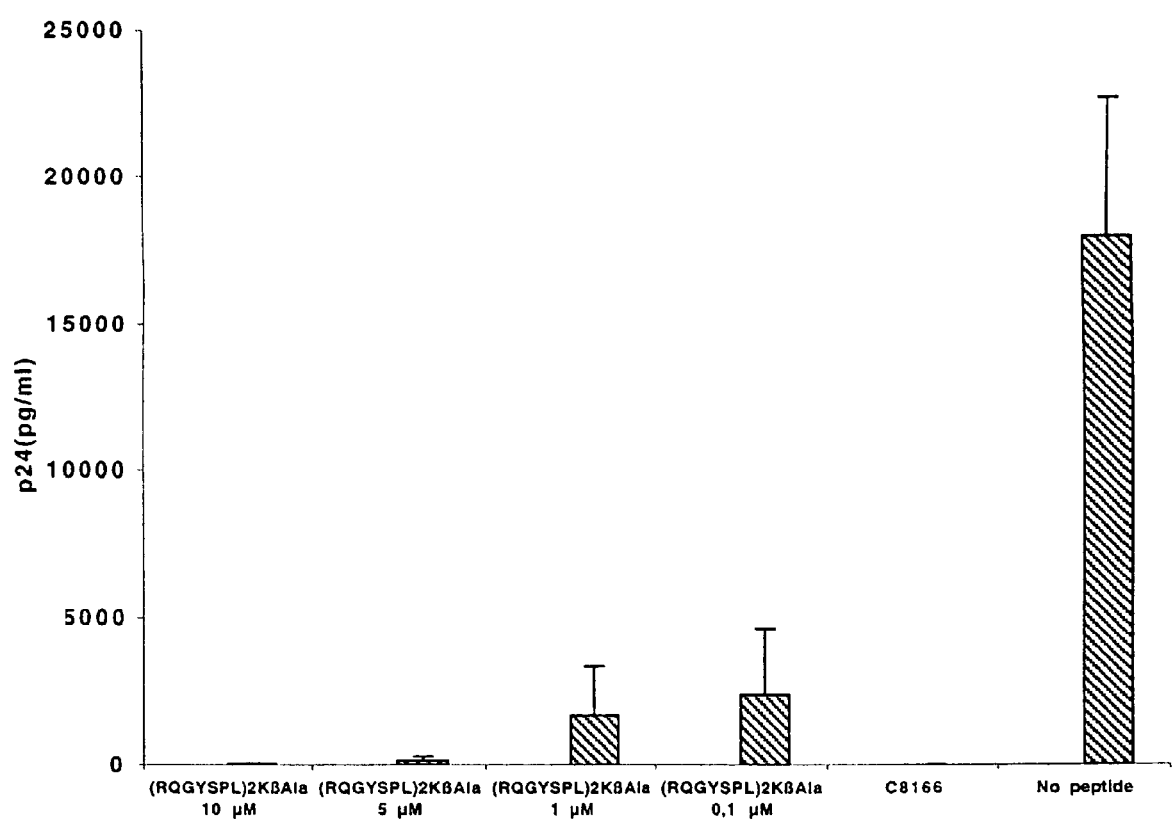
FIG. 1A is a graph depicting HIV-1 infection rates in the presence of an invented MBPC at various concentrations, in accordance with features of the present invention.

The inventors have now discovered further MBPCs which are effective as treatments for HIV infections. These MBPCs use peptides derived from the HIV envelope transmembrane glycoprotein gp41. The amino acid sequences of these MBPCs were selected on the basis of sequence homologies between various HIV isolates. The choice of gp41 amongst viral proteins was based on the following:

i) the importance of this domain in the virus-cell and cell-cell fusion processes leading to virus entry into the host cell, ii) the importance of the gp160 splicing into gp120 and gp41 for the fusogenic activity to take place, iii) the existence of neutralizing anti-gp41 antibodies, e.g. antibody 2F5, and iv) the existence of a unique disulphide bridge, in contrast to gp120, which makes it easier to obtain peptides mimicking specific conformational domains of gp41.

It is presumed that the gp41-derived MBPCs of this invention interfere with a critical step of the fusion process.

The invention provides a multiple branch peptide construction and a method for the therapeutic treatment of patients with HIV infections. The multiple branch peptide construction comprises a core matrix to which are bonded from 2 to 16, and preferably from 2 to 8 peptides, each of which comprises the sequence RQGY (SEQ. ID. NO. 1) preceded by from 0 to 4 amino acid residues and succeeded by from 0 to 4 amino acid residues. Most preferably, the peptides bonded to a two-branched core matrix are RQGYS (SEQ. ID. NO. 2). The method for the therapeutic treatment of patients with HIV infections comprises administering such an MBPC to the patient, preferably in such an amount as to induce in the patient a blood concentration of the MBPC of from $10^{-7}$ to $10^{-4}$ molar.

The core matrix is a dendritic polymer which is branched in nature, preferably with each of the branches thereof being identical. The core matrix is based on a core molecule which has at least two functional groups to which molecular branches having terminal functional groups are covalently bonded. Suitable core molecules include ammonia or ethylene diamine. Suitable molecular branches include acrylic ester monomers which are polymerized onto the core molecule. Such molecules may be created to present varying number of branches, depending on the number of monomers branched from the core molecule. The preferred core molecule is lysine. A central lysine residue is bonded to two lysine residues, each through its carboxyl group, to one of the amino groups of the central lysine residue. This provides a molecule with four amino groups, which may be the core matrix for an MBPC having four peptides.

Alternatively, one can provide a molecule with eight branches by bonding four lysine residues through their carboxyl groups to one of the amino groups of the lysine residues which are attached to the central lysine. This molecule can serve as the core matrix for an MBPC having eight peptides or can alternatively receive eight lysine residues to form a core matrix for an MBPC having sixteen peptides.

The C-ends of peptides are covalently bonded to each of the branches of the core matrix to form the MBPC. The peptides may be the same, which is preferred, or may be different from one another. The resulting molecule has a cluster of peptides at the surface and an interior core matrix which is not presented and is therefore not antigenic.

Spacers may, if desired, be included between the peptides and the core matrix. The carboxyl group of the first lysine residue may be left free, amidated, or coupled to β-alanine or another blocking compound.

Peptides can include D or L-amino acid residues. D amino acids last longer in vivo because they are harder for peptidase to cut, but the L amino acids have better activity, as discussed below.

Moreover, peptide analogues, synthetic constructs using the carbon skeleton of peptides but omitting the —CONH— peptide bonds, can be employed in place of peptides. Thus, it should be understood that references to peptides herein may also be taken to include peptide analogues. It is believed that peptide analogues will be more resistant to peptidase and last longer in vivo.

If the peptide is too long, the MBPC will become antigenic. It is therefore desirable that each peptide should have not more than ten, and preferably not more than nine, amino acid residues.

The preferred MBPCs for use in this invention are as follows:

1. $(RQGYSPL)_8-(K)_4-(K)_2-K-\beta A-OH$, (SEQ. ID. NO. 3) and has a short hand designation of "RL.1";
2. $(RQGYSPL)_{16}-(K)_8-(K)_4-(K)_2-K-\beta A-OH$, (SEQ. ID. NO. 4) and has a short hand designation of "RL.2";
3. $(RQGYS)_2-K-\beta A-OH$, (SEQ. ID. NO. 5) and has a short hand designation of "Short RL";
4. $(RQGYSPL)_2-K-\beta A-OH$, (SEQ. ID. NO. 6);
5. $(RQGY)_8-(K)_4-(K)_2-K-\beta A-OH$ (SEQ. ID. NO. 7).

The OH terminal shown above on the β-alanine indicates the carboxyl group thereof, with the amino group being attached to the carboxyl group of the lysine residue. The carboxyl group of the β-alanine may alternatively be modified to form a carboxamide terminal.

The preparation of the MBPCs of the invention, having a branched core with peptides attached thereto, can be effected by methods known in the art, see e.g. Tam et al, J. Immun. 148, 914-920 (1992). Preferably, for small quantities (under one kilogram), a solid phase method is used to obtain the MBPCs. Stepwise assembly of the peptide chains can be carried out automatically on 4-(oxymethyl)-phenylacetamidomethyl copoly(styrene-1% divinyl benzene).

The Boc/benzyl strategy may be used, including a systematic double coupling scheme with hydroxybenzotriazole active esters (Boc-amino-acid-OBt). The final cleaving from resin is effected with strong acid, such as anhydrous hydrogen fluoride (1 hour at 0° C.). The MBPC is then washed with diethyl ether and solubilized in water. After lyophilization, the MBPC may be pre-purified on a P2 or G15 type molecular filtration column, equilibrated with 0.1N acetic acid. The eluate fraction may then be recovered. The purification step is achieved by using $C_8$ or $C_{18}$ reversed-phase HPLC. The MBPC may be characterized by its amino acid content after acid hydrolysis (6N HCl, 115° C., 24 hours) and electro-spray mass spectrometry.

The gp41-derived MBPCs of the invention have been tested in vitro for their ability to inhibit HIV-induced syncytium formation, and infection of human lymphocytes by both HIV-1 and HIV-2 viruses (several laboratory strains including LAV-2B, an HIV-2 virus able to infect some CD4−/GalCer− cells, as well as clinical isolates such as JRCSF, P16/B6 and P16/C9). The diverse peptide constructions were found to be inactive, except for MBPC RL1 which possessed potent antiviral properties in all tests. By contrast, the monomeric RQGYSPL (Seq. Id. No. 6) was found to be inactive. Some results are shown in Tables 1 and 2 below. Similar results were obtained with other HIV strains and clinical isolates tested so far.

The MBPC RL1 showed neither cellular toxicity nor lethal activity when injected by the intra-cerebroventricular route in both C57/BL6 and Balb-C mice (concentration tested was $3\times10^{-3}$ M, corresponding to 100 μg of peptide injected per 20 g mouse).

Surprisingly and unexpectedly, the inventors have found that certain MBPCs are extremely effective when only two branches are attached to the core matrix molecule. These two-branched moieties, designated herein as MP2 RL, contain better anti-viral activity than the 8-branched MBPC variety discussed supra, and in U.S. patent application Ser. No. 09/342,847, incorporated herein by reference.

A salient feature of the MP2 RL constructs is the presence of the four-amino-acid long peptide RQGY (Seq. Id. No. 1). A preferred iteration of the peptide is where a serine is covalently attached to the tyrosine to yield the five-amino-acid long peptide RQGYS (Seq. Id. No. 2).

As can be seen in Table 3, MBPC containing the RQGYS (Seq. Id. No. 2) peptide render superior HIV inhibition characteristics. This is true whether the peptide contains solely the five peptides (as depicted as peptide number 2 in the Table) or when the peptide contains more than the five peptides (as depicted as peptide number 11 in Table 3).

Figure 1B:
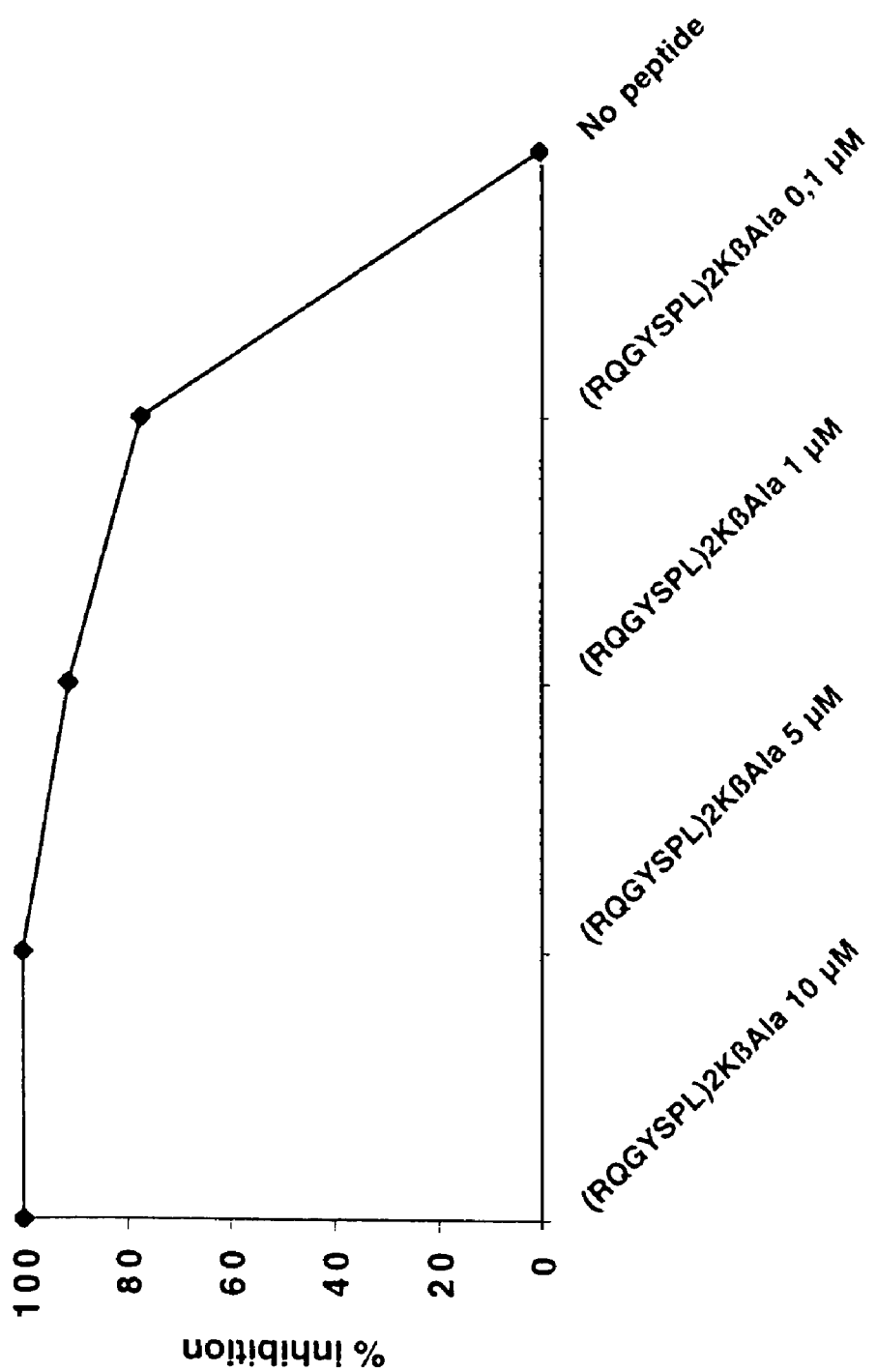
FIG. 1B is a graph depicting various inhibition percentages of the invented MBPC, in accordance with features of the present invention.
Figure 2:
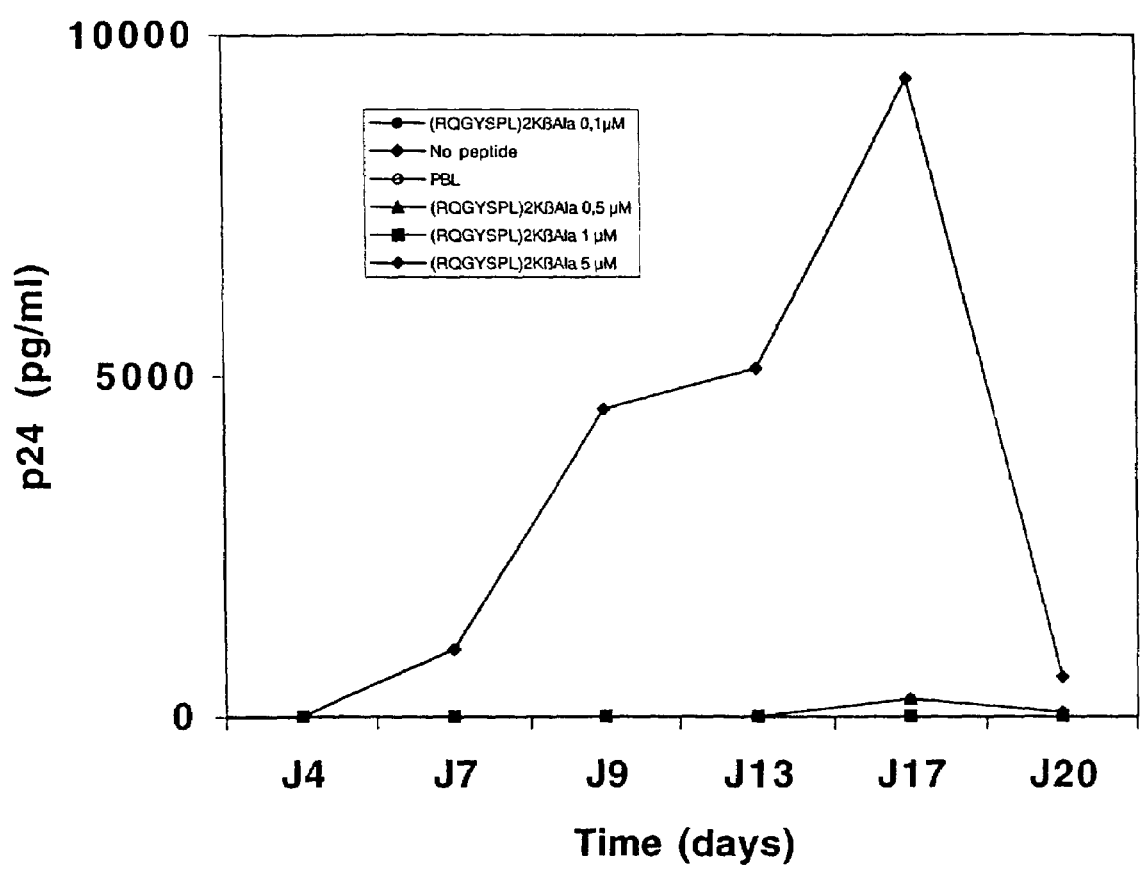
FIG. 2 is a graph depicting the efficacy of an invented MBPC to prevent PBMC infection, in accordance with features of the present invention.

FIGS. 1-2 depict the surprising efficacy of the two-peptide-branch construct utilizing the peptide branch RQGYSPL (Seq. Id. No. 6). FIG. 1 shows that even at 0.1 micro-molar (μm) concentrations of the MBPC, viral activity is one tenth that seen in controls. Specifically, marked inhibition of syncytium formation and p24 production on HIV-1$_{NL403}$ nfected C8166 cells was noted. Also, no viral activity is seen at 10 μm concentrations and virtually no activity at 5 μm. It should be noted that concentrations are in relation to blood or serum in which the cells are suspended.

FIG. 2 shows that at a concentration of 0.1 μM, the MBPC construct $(RQGYSPL)_2K-\beta A$ (Seq. Id. No. 15) inhibits 100 percent of HIV-1$_{NL403}$ infected Peripheral Blood Mononuclear Cells (PBMCs).

The inventors also found that the MBPC (D-LPSYGQR)$_8$-K4-K2-K-βA (Sep. Id. No. 17) can totally inhibit HIV infection of PBMCs and C8166 cells at a concentration of 1 μM and 0.1 Mm.

Further, the MBPC (RQGY)8-K4-K2-K-βA (Seq. Id. No. 7) and (LPSYGQR)$_8$-K4-K2—K-βA (Seq. Id. No. 17) inhibit syncytium formation and p24 production of HIV-infected cells, with 100 percent inhibition occurring at 5 μM.

The multi-branched peptides were not toxic for all cells, even at concentrations of 50 μM.

Materials

N-α-fluorenylmethyloxycarbonyl (Fmoc) amino acid derivative were purchased from Perkin-Elmer. All solvents were analytical-grade commercial products from Perkin Elmer or SDS (Peypin, France).

Human peripheral blood lymphocytes (PBLs) obtained from healthy HIV-seronegative donor (Etablissement Francais du Sang, Marseille, France) were isolated by ficoll-Hypaque gradient centrifugation. Cells were cultured in R10 medium supplemented with 20 units/ml of interleukin-2 (IL-2, Proleukin, Chiron, The Netherlands). R10 medium consists of RPMI 1640 supplemented with 2 mM ultra-glutamine (BioWhittaker, Vervires, Belgium), penicillin (100 units/ml), streptomycin (100 μg/ml), and 10% heat-inactivated fetal calf serum (BioWhittaker). Cells were first stimulated with phytohemaggiutinin (20 μg/ml)-supplemented R10 (PHAP, DIFCO, Detroit, Mich., USA) for three days. Then, the medium was replaced with R10 supplemented with IL2 (20 units/ml), and subsequently cultures and experiments were carried out in this medium in a 37° C. humidified incubator with 5% $CO_2$.

Viral stocks of the TCLA X4 HIV-1$_{NL4-3}$ (obtained from I. Hirsh, INSERM U 372, Marseille, France) (Adachi et al., 1986; Barre-Sinoussi et al., 1983) were produced in permissive CEM cells. HIV-1$_{HX10}$ and HIV-1$_{MN}$ (obtained from Q. Sattentenau) were propagated in H9 cells. Cultured supernatants from infected cells were collected at the peak of maximal viral production as assessed by p24 assay, and residual cells were removed by centrifugation at 4° C. (2,000 rpm/5 min). They were sampled and stored at −80° C. The viral stock infectious titer (50% tissue culture infectious dose, $TCID_{50}$) was established on C8166 cells and PBL.

Chemical Synthesis and Characterisation

Detail of Synthetic MBPCs

Stepwise elongation of MBPCs was carried out on 0.1 mmol of β-Ala-Wang resin. (0.38 mequiv. of amino group/g) using an automatic peptide synthesizer (Applied Biosystems Inc.) Trifunctional amino acids were protected on their side-chain as follows: trityl (Trt) for Gln; t-butyl (t-Bu) for Ser and Tyr, Fmoc for Lys and pentamethylchroman (Pmc) for Arg. The purity of peptides was verified by: (i) analytical reverse-phase HPLC (ii) amino acid hydrolysis (6 N HCl/1% phenol (mass/vol.), 20 h, 120° C., N2 atmosphere), and (iii) mass determination by matrix-assisted laser desorption ionization-time of flight (MALDI-TOF) mass spectrometry.

$HIV_{NL4-3}$ Infection

Detail of C8188 Cells

C8188 cells were infected with HIV to establish a baseline control. Similar C8188 cells were pretreated the invented MBPCs and then subjected to HIV to determine inhibition rates. The results are illustrated in FIGS. 1A, 1B and 2.

Samples of $3 \times 10^5$ C8166 cells were placed in 96-well plates in a volume of 100 μl of culture medium containing various concentrations of peptide. After a one hour treatment at 37° C., 100 μl of viral solution of $HIV-1_{NL4-3}$ were added. The cells were exposed to the virus of one hour at 37° C. at a multiplicity of infection of 1,000 $TCID_{50}$ per ml. After through washing, cells were replaced in 1 ml of R10 with the treatment in 24-well plates and cultured in a 37° C. incubator. C8166 culture medium was replaced at day-4 post-infection. During this assay, treatment with peptide was permanent (before, during and after infection). Assays on C8166 cells have been performed at least twice and in duplicate. Toxicity was evaluated by daily cell count and trypan-blue exclusion assay. Infection of C8166 T-Cells with $HIV-1_{NL4-3}$ was assessed by virus-induced cytopathic effect (syncytia formation) and by quantification of p24 viral protein in the culture supernatants. Measurements of HIV-1 $p24^{gag}$ concentrations in the culture supernatants were achieved by ELISA, with a detection cut-off of 5 pg/ml (p24 HIV kit, NEN Dupont, Belgium; Quanti-Kine software, RILAB, Genova, Italy).

Infection Detail of Human PBLs

Samples of $10^6$ human PBLs were placed in 96-well plates in 100 μl of R10 containing various concentrations of peptide. After one hour treatment of 37° C., 100 μl of viral solution of $HIV-1_{NL4-3}$ were added. The cells were exposed to the virus for one hour at 37° C. flushed with 5% $CO_2$. The PBL culture medium was replaced every 3-4 days. The cell viability was assessed by cell counts and trypan-blue exclusion assay. The viral production in the culture supernatant was quantified by p24 ELISA test, as described supra. All the experiments have been done in blind-tests. Tests have been achieved in duplicate.

TABLE 1

Inhibition of the H × 10 (HIV-1) strain infectivity by the MBPCs RL1 and SPC3

| Peptides | Molarity | OD | p24 (ng/ml) | Inhibition (%) |
|---|---|---|---|---|
| SPC3-D4 | $5 \times 10^{-5}$ | 0.052 | 0.05556143 | 98.89 |
|  | $1 \times 10^{-5}$ | 0.211 | 0.48654334 | 89.13 |
|  | $5 \times 10^{-6}$ | 0.849 | 2.21589212 | 50.78 |
|  | $1 \times 10^{-6}$ | 1.797 | 4.78552009 | 0 |
| SPC3-D5 | $5 \times 10^{-5}$ | 0.066 | 0.09350952 | 98.47 |

TABLE 1-continued

Inhibition of the H × 10 (HIV-1) strain infectivity by the MBPCs RL1 and SPC3

| Peptides | Molarity | OD | p24 (ng/ml) | Inhibition (%) |
|---|---|---|---|---|
| RL1-D4 | $5 \times 10^{-5}$ | 0.047 | 0.04200854 | 99.09 |
|  | $1 \times 10^{-5}$ | 0.359 | 0.88770888 | 79.82 |
|  | $5 \times 10^{-6}$ | 0.657 | 1.69546114 | 61.45 |
|  | $1 \times 10^{-6}$ | 1.148 | 3.02635495 | 31.29 |
| RL1-D5 | $5 \times 10^{-5}$ | 0.035 | 0.00948160 | 99.75 |

SPC3 is $(GPGRAF)_8-(K)_4-(K)_2-K-\beta A-OH$ as disclosed in WO95/07929.

D4 and D5 refer to days 4 and 5 of the experiment.

OD stands for Optical Density.

N.B. Experiments were performed with non diluted virus solution.

TABLE 2

Inhibition (%) of clinical isolates infectivity by the MBPCs RL1 and SPC3.

| [conc] | $1 \times 10^{-5}$ | $5 \times 10^{-6}$ | $1 \times 10^{-6}$ | $5 \times 10^{-7}$ | $1 \times 10^{-7}$ | $5 \times 10^{-8}$ |
|---|---|---|---|---|---|---|
| SPC3 | 85.7 | 50.0 | 28.6 | 0 | 0 | 0 |
| RL1 | 89.3 | 70.0 | 67.1 | 40.8 | 18.3 | 0 |

Example shown is the HIV-1 W5A2A9 isolate.

N.B. Experiments were performed with non-diluted virus solution.

TABLE 3

Inhibition of HIV-1 Infection C8166 cells by RL MP2 analogs

| | | P24 (pg/ml) | | Syncytium formation | |
|---|---|---|---|---|---|
| Peptide[1] | | 1 μm | 10 μm | 1 μm | 10 μm |
| 1. $(RQGYSP)_2-K-\beta A$ | (Seq. Id. No. 8) |  |  | + | − |
| 2. $(RQGYS)_2-K-\beta A$ | (Seq. Id. No. 5) | 0 | 0 | − | − |
| 3. $(RQGY)_2-K-\beta A$ | (Seq. Id. No. 9) |  |  | ± | ± |
| 4. $(RQG)_2-K-\beta A$ | (Seq. Id. No. 10) |  |  | ± | − |
| 5. $(QGYSPL)_2-K-\beta A$ | (Seq. Id. No. 11) |  |  | ± | − |
| 6. $(GYSPL)_2-K-\beta A$ | (Seq. Id. No. 12) |  |  | ± | ± |

TABLE 3-continued

Inhibition of HIV-1 Infection C8166 cells by RL MP2 analogs

| Peptide[1] | | P24 (pg/ml) | | Syncytium formation | |
|---|---|---|---|---|---|
| | | 1 μm | 10 μm | 1 μm | 10 μm |
| 7. (YSPL)$_2$-K-βA | (Seq. Id. No. 13) | | | ± | ± |
| 8. (SPL)$_2$-K-βA | (Seq. Id. No. 14) | | | ++ | ± |
| 9.[2] (D RQGYSPL)$_2$-K-βA | | | | ++ | ++ |
| 10. (KQGYSPL)$_2$-K-βA | (Seq. Id. No. 16) | | | ++ | ++ |
| 11. (RQGYSPL)$_2$-K-βA | (Seq. Id. No. 8) | 0 | 0 | – | – |
| 12. (AcRQGYSPL)$_2$-K-βA | (Seq. Id. No. 17) | | | ++ | ++ |
| 13. AZT | | 0 | 0 | – | – |
| 14. No Peptide | | 25000 | 23000 | ++ | ++ |

[1]Peptide concentrations are in micro-Moles (μM).
[2]Seq. Id. No. 15
Symbols:
"++" = number of syncytia present in the well were similar to that in control untreated well (35 to 40 syncitia per well);
"–" = total absence of syncitia in the well;
"±" = presence of 1 to 3 syncitia in the well.

While the invention has been described with reference to details of the illustrated embodiment, these details are not intended to limit the scope of the invention as defined in the appended claims.

The embodiment of the invention in which an exclusive property or privilege is claimed is defined as follows:

1. A multiple branch peptide construct comprising a plurality of peptides limited to 10 or less amino acids, each of the peptides containing the amino acid sequence RQGY (Seq. Id No. 1) preceded by 0 to 4 amino acid residues and succeeded by from 0 to 1 amino acid residues, and wherein the peptides are attached to a core matrix.

2. The construct as recited in claim 1 wherein each peptide is the same.

3. The construct as recited in claim 1 wherein each peptide consists of RQGYS (Seq. Id. No. 2).

4. The construct as recited in claim 1 wherein each peptide includes not more than 8 amino acids.

5. The construct as recited in claim 1 wherein the core matrix is comprised of lysine residues.

6. The construct as recited in claim 5 wherein the core matrix contains a K-βA moiety, wherein βA is beta alanine.

7. The construct as recited in claim 1 wherein spacers exist intermediate the core matrix and the peptides.

8. The construct as recited in claim 1 wherein the peptides include at least one D-amino acid residue.

9. The construct as recited in claim 1 wherein said construct is nonimmunogenic at a blood concentration of up to $10^{-4}$ molar.

10. The construct as recited in claim 1 wherein said construct is combined with a pharmaceutically acceptable carrier to form a medicament.

11. A multiple branch peptide construct comprising two peptides, each of the peptides containing the amino acid sequence RQGY (Seq. Id. No. 1) preceded by 0 to 4 amino acid residues and succeeded by from 0 to 1 amino acid residues and wherein the peptides are attached to a core matrix.

12. A multiple branch peptide construct comprising two peptides, wherein each of the peptides is RQGYS (Seq. Id. No. 2) and the peptides are attached to a core matrix containing a K-βA moiety, wherein βA is beta alanine.

13. A multiple branch peptide construct having the formula $(RQGYS)_2$-K-βA (Seq. Id. No. 5).

14. The construct as recited in claim 11 having the formula $(RQGY)_8$-$(K)_4$-$(K)_2$-K-βA (Seq. Id. No. 7).

15. The construct as recited in claim 12 having the formula $(RQGYS)_2$-K-βA-OH (SEQ. ID. NO. 5).

* * * * *